United States Patent
Chattaraj et al.

(10) Patent No.: US 11,844,930 B2
(45) Date of Patent: Dec. 19, 2023

(54) USER-MOUNTABLE ELECTRONIC DEVICE WITH ACCELEROMETER-BASED ACTIVATION FEATURE

(71) Applicant: MEDTRONIC MINIMED, INC., Northridge, CA (US)

(72) Inventors: Sarnath Chattaraj, Simi Valley, CA (US); Hsi Fusselman, Simi Valley, CA (US); Davy Tong, Thousand Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 576 days.

(21) Appl. No.: 17/084,471

(22) Filed: Oct. 29, 2020

(65) Prior Publication Data

US 2022/0133998 A1  May 5, 2022

(51) Int. Cl.
*A61M 5/172* (2006.01)
*G01P 15/00* (2006.01)
*A61M 5/158* (2006.01)

(52) U.S. Cl.
CPC ... *A61M 5/1723* (2013.01); *A61M 2005/1585* (2013.01); *A61M 2005/1726* (2013.01); *A61M 2205/33* (2013.01); *A61M 2230/201* (2013.01); *G01P 15/00* (2013.01)

(58) Field of Classification Search
None
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |

(Continued)

*Primary Examiner* — Manuel A Mendez
(74) *Attorney, Agent, or Firm* — Foley & Lardner LLP (57) ABSTRACT

A user-mountable electronic device includes a housing, an accelerometer located within the housing, and at least one processor located within the housing. The accelerometer measures acceleration of the user-mountable electronic device and is configured to generate an output in response to detecting acceleration of the user-mountable electronic device that is greater than a minimum acceleration threshold. The at least one processor controls operation of the user-mountable electronic device. The at least one processor is configured to receive the output generated by the accelerometer and, in response thereto, to transition from a dormant or standby state of the user-mountable electronic device to an active state of the user-mountable electronic device.

20 Claims, 3 Drawing Sheets

(56) References Cited

U.S. PATENT DOCUMENTS

| | | | |
|---|---|---|---|
| 6,558,351 B1 * | 5/2003 | Steil | A61M 5/14244 |
| | | | 604/522 |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 3,181,849 A1 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2017/0281000 A1 * | 10/2017 | Wedekind | G16H 40/60 |
| 2019/0342637 A1 * | 11/2019 | Halac | A61B 5/14546 |

* cited by examiner

USER-MOUNTABLE ELECTRONIC DEVICE WITH ACCELEROMETER-BASED ACTIVATION FEATURE

TECHNICAL FIELD

The present technology is generally related to an electronic device that is affixed to, mounted to, inserted into, or otherwise deployed onto the body of a patient.

BACKGROUND

A variety of personal or portable electronic devices are intended for application to the body or skin of a user. For example, electronic medical devices (such as physiological characteristic or analyte sensors, monitor devices, fluid infusion pumps, and activity monitors) can be designed as user-mounted or user-attached devices. In this regard, analyte sensors have been designed for use in obtaining an indication of blood glucose (BG) and subcutaneous sensor glucose (SG) levels and monitoring glucose levels in a diabetic patient, with the distal segment portion of the sensor positioned subcutaneously in direct contact with patient extracellular fluid.

A device with a glucose sensor of the type described above may be packaged and sold as an assembled product that includes certain features or components that allow the patient to position, deploy, and subcutaneously implant the sensor. For example, glucose sensors are often implanted subcutaneously/transcutaneously using a needle that punctures the skin of the patient as the sensor is deployed and forced onto the body. The glucose sensor device is compatible with an deployment or insertion device that cooperates with an insertion needle to insert the sensor.

Some user-mountable electronic devices are initially provided in a dormant or low power state to extend shelf life and battery life. After deployment onto the body of the user, the devices are switched from the dormant state to a default operating state that consumes an ordinary amount of operating power.

Accordingly, it is desirable to have a low-cost and reliable mechanism and methodology to detect deployment of a user-mountable electronic device for purposes of transitioning from a low power state to a default operating state. Furthermore, other desirable features and characteristics will become apparent from the subsequent detailed description and the appended claims, taken in conjunction with the accompanying drawings and the foregoing technical field and background.

BRIEF SUMMARY

The subject matter of this disclosure generally relates to user-mountable devices, such as a device with a continuous glucose monitoring (CGM) sensor that is inserted into the subcutaneous tissue. Such devices are typically battery powered and have a designated shelf life. Such devices are typically wirelessly connected to an infusion pump so that the patient may monitor his/her glucose levels. For closed-loop systems, the pump uses the glucose readings to determine the appropriate insulin dosage. Prior to deployment, it is desirable for the device to consume the smallest amount of power possible in order to meet or exceed its labeled shelf life. To achieve this goal, the device must know when it has been deployed so that it does not unnecessarily expend power attempting to connect to a pump.

In one aspect, the present disclosure provides a user-mountable electronic device having: a housing; an accelerometer to measure acceleration of the user-mountable electronic device, the accelerometer located within the housing, and the accelerometer configured to generate an output in response to detecting acceleration of the user-mountable electronic device that is greater than a minimum acceleration threshold; and at least one processor to control operation of the user-mountable electronic device. The at least one processor is located within the housing, and the at least one processor is configured to receive the output generated by the accelerometer and, in response thereto, to transition from a dormant or standby state of the user-mountable electronic device to an active state of the user-mountable electronic device.

In another aspect, the disclosure provides a system having: a user-mountable electronic device that is deployable onto a body part of a user; and a deployment device that is compatible with the user-mountable electronic device. The user-mountable electronic device includes: a housing; an accelerometer to measure acceleration of the user-mountable electronic device, the accelerometer located within the housing, and the accelerometer configured to generate an output in response to detecting acceleration of the user-mountable electronic device that is greater than a minimum acceleration threshold; and at least one processor to control operation of the user-mountable electronic device. The at least one processor is located within the housing, and the at least one processor is configured to receive the output generated by the accelerometer and, in response thereto, to transition from a dormant or standby state of the user-mountable electronic device to an active state of the user-mountable electronic device. The deployment device is actuatable to move the user-mountable electronic device toward the body part of the user with a deployment acceleration that exceeds the minimum acceleration threshold. The acceleration is utilized to detect acceleration of the user-mountable electronic device that is indicative of deployment.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be configurable to be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a user-mountable electronic device, such as a medical device or component, that is designed to be affixed to the body of a user. In this regard, the electronic device is deployable onto a body part of the user via, for example, a suitably configured deployment device that is compatible with the electronic device. The electronic device is initially provided in a dormant or standby state (e.g., a low power or reduced power consumption state) to extend shelf life prior to usage. The electronic device is placed and affixed onto the body of the user during a deployment action using, e.g., a compatible deployment device that quickly moves the electronic device toward the body. The electronic device has an onboard accelerometer to measure or detect acceleration of the electronic device during the deployment action. The accelerometer is calibrated or otherwise configured to detect a deployment acceleration that exceeds a minimum acceleration threshold (that is indicative of the deployment action). Detection of the deployment acceleration causes the electronic device to transition from the dormant or standby state to an active state (e.g., a high power or normal power consumption state). In other words, the accelerometer triggers the activation, initialization, or "wake up" of the electronic device, such that the electronic device can proceed with its normal mode of operation.

In accordance with certain embodiments, the user-mountable electronic device includes or is realized as an analyte sensor that measures a physiological characteristic of the user, such as blood glucose. In accordance with some embodiments, the user-mountable electronic device is realized as a single component that includes: (1) an analyte sensor that measures a physiological characteristic of the user; and (2) a medicament delivery element, such as a fluid delivery cannula, conduit, or needle. In accordance with some embodiments, the user-mountable electronic device is realized as a single component that includes: (1) an analyte sensor that measures a physiological characteristic of the user; (2) a medicament delivery element, such as a fluid delivery cannula, conduit, or needle; and (3) a fluid pump mechanism or system that is electronically controlled to regulate the delivery of a medicament to the user via the fluid delivery cannula, conduit, or needle. In this context, the user-mountable electronic device may be a component of a system used to treat diabetes (more specifically, a continuous glucose sensor with wireless communication capability, an insulin infusion device, or a blood glucose meter/monitor), although embodiments of the disclosed subject matter are not so limited. For the sake of brevity, conventional features and characteristics related to infusion systems, analyte sensors such as continuous glucose sensors, and fluid conduits such as soft cannulas may not be described in detail here.

The user-mountable electronic device may include one or more elements or components that are intended for insertion into or application onto the body of the user. For example, the electronic device may include an analyte sensor that is designed to be inserted into the skin of the user. In certain embodiments, the electronic device includes or is realized as a continuous glucose sensor that is insertable into the user to obtain sensor glucose measurements. Accordingly, actuation of the deployment device initiates insertion of the analyte sensor into the user. As another example, the electronic device may be implemented as a fluid infusion device having a fluid delivery cannula or needle that is designed to be inserted into the skin of the user. In certain embodiments, the electronic device includes a fluid delivery cannula that is insertable into the user to deliver insulin from a fluid reservoir to the user. Accordingly, actuation of the deployment device initiates insertion of the fluid delivery cannula or needle into the user.

In certain embodiments, the user-mountable electronic device is realized as (or include) a transdermal medicament delivery device that is configured to deliver a medicament to the user through the skin without using an inserted needle, cannula, or conduit. Similarly, the user-mountable electronic device may be realized as (or include) a transdermal analyte sensor device that is configured to detect or measure a physiological characteristic of the user through the skin or via contact with the skin, without using an inserted sensor element, electrode, or lead. As additional examples, the user-mountable electronic device may include or be realized as any of the following, without limitation: a body temperature monitor; a heartrate monitor; a pulse oximeter; a sweat sensor; and/or an activity tracker. A user-mountable electronic device of this type may include an adhesive strip or component that secures the device to the skin of the user after deployment. In some embodiments, the user-mountable electronic device is realized as an implantable device that is injected or implanted into the body of the user via the application of force that results in a detectable deployment acceleration.

Figure 1:
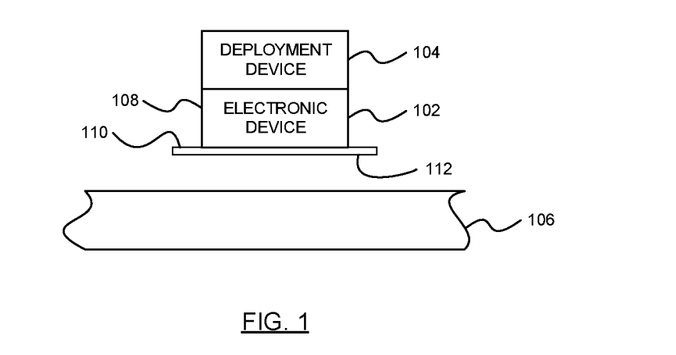
FIG. 1 is a block diagram representation of a user-mountable electronic device and a compatible deployment device, prior to deployment of the electronic device onto the body of the user.
Figure 2:
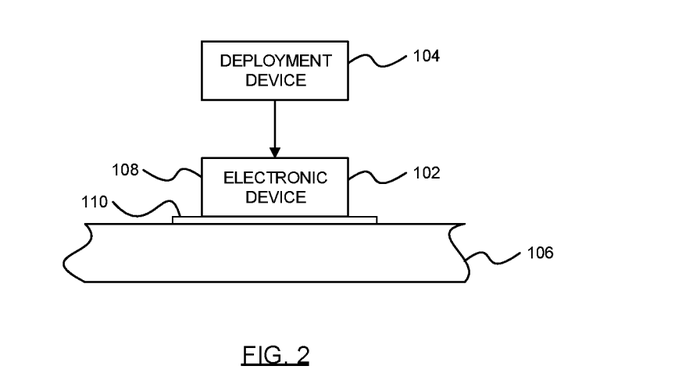
FIG. 2 is a block diagram representation of the electronic device and the deployment device, during deployment of the electronic device onto the body of the user.
Figure 3:
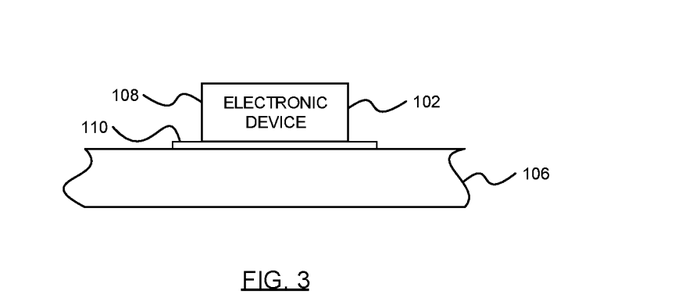
FIG. 3 is a block diagram representation of the electronic device after deployment onto the body of the user.

Referring to the drawings, FIG. 1 is a block diagram representation of a user-mountable electronic device 102 and a compatible deployment device 104, prior to deployment of the electronic device 102 onto a body part 106 of the user. FIG. 2 is a block diagram representation of the electronic device 102 and the deployment device 104, during deployment of the electronic device 102 onto the body part 106 of the user, and FIG. 3 is a block diagram representation of the electronic device 102 after deployment onto the body part 106 of the user. The electronic device 102 includes a housing 108 that covers, encloses, or otherwise protects its internal components. The electronic device 102 may include an adhesive patch 110 (or any suitably configured adhesive element or component) on a bottom surface of the housing 108. The adhesive patch 110 may be provided with a removable liner (not shown) that is removed to reveal an exposed adhesive surface 112 of the adhesive patch 110, as depicted in FIG. 1. In certain embodiments, the electronic device 102 and the deployment device 104 are coupled together as a unit before actuation of the deployment device (see FIG. 1). In this regard, the electronic device 102 and the deployment device 104 can be manufactured, assembled, and packaged as a combined unit that is appropriate for storage, shipping, and handling. Alternatively, the electronic device 102 and the deployment device 104 can be individually offered as separate (but compatible) components that require assembly or loading before deployment of the electronic device 102 onto the body part 106.

As schematically depicted by the downward pointing arrow in FIG. 2, actuation, triggering, or activation of the deployment device 104 moves the user-mountable electronic device 102 toward the body part 106 of the user. The deployment device 104 includes at least one spring, a pneumatic feature, a pre-tensioned structure, or equivalent structure that imparts downward force to the electronic device 102 when the deployment device 104 is actuated. For example, the deployment device 104 and the electronic device 102 may be provided in a pre-loaded state that is ready to deploy, or it may be necessary for the user to manipulate the deployment device 104 and/or the electronic device 102 into a loaded state before deployment. As one non-limiting example, the deployment device 104 can be configured and implemented in accordance with the insertion mechanism provided with the MINIMED MIO ADVANCE infusion set offered by MEDTRONIC. As another non-limiting example, the deployment device 104 can be configured and implemented in accordance with the MINIMED QUICK-SERTER insertion device offered by MEDTRONIC. As another non-limiting example, the deployment device 104 can be configured and implemented in accordance with the MINIMED SIL-SERTER insertion device offered by MEDTRONIC. As another non-limiting example, the deployment device 104 can be configured and implemented in accordance with the insertion mechanism provided with the MINIMED MIO infusion set offered by MEDTRONIC. These and other currently available insertion devices or mechanisms are suitable for use as the deployment device 104 disclosed here.

Actuation of the deployment device 104 releases the electronic device 102 such that it moves toward the body part 106 with a deployment acceleration that is sufficient to adhere the adhesive surface 112 (of the adhesive patch 110) to the body part 106. In this regard, actuation of the deployment device 104 moves the exposed adhesive surface 112 of the adhesive patch 110 into contact with the body part 106 to affix the user-mountable electronic device 102 to the body part 106. If the electronic device includes an insertable analyte sensor, an insertable fluid delivery cannula, and/or another insertable component, then the deployment acceleration is also sufficient to facilitate insertion of such insertable component(s) into the body part 106.

FIG. 3 shows the electronic device 102 by itself after deployment onto the body part 106. The deployment device 104 is decoupled and removed from the electronic device 102 after it has been actuated. In certain embodiments, the deployment device 104 retains one or more insertion needles that retract after insertion of the analyte sensor and/or the fluid delivery cannula. Accordingly, the deployment device 104 may be discarded after the electronic device 102 has been attached to the body part 106.

As mentioned above, the electronic device 102 operates in the dormant or standby state before actuation of the deployment device 104 (while the electronic device 102 and the deployment device 104 are coupled together as a unit). Accordingly, in FIG. 1, the electronic device 102 is in the dormant or standby state. Actuation of the deployment device 104 causes the electronic device 102 to accelerate toward the body part 106. The accelerometer onboard the electronic device 102 detects acceleration that is greater than a minimum acceleration threshold and, in response thereto, the electronic device 102 transitions from the dormant or standby state to the active state. The deployment device 104 decouples from the electronic device 102 after actuation of the deployment device 104, and the electronic device 102 continues to operate in the active state after actuation of the deployment device 104. Accordingly, in FIG. 3, the electronic device 102 is in the active state.

Figure 4:
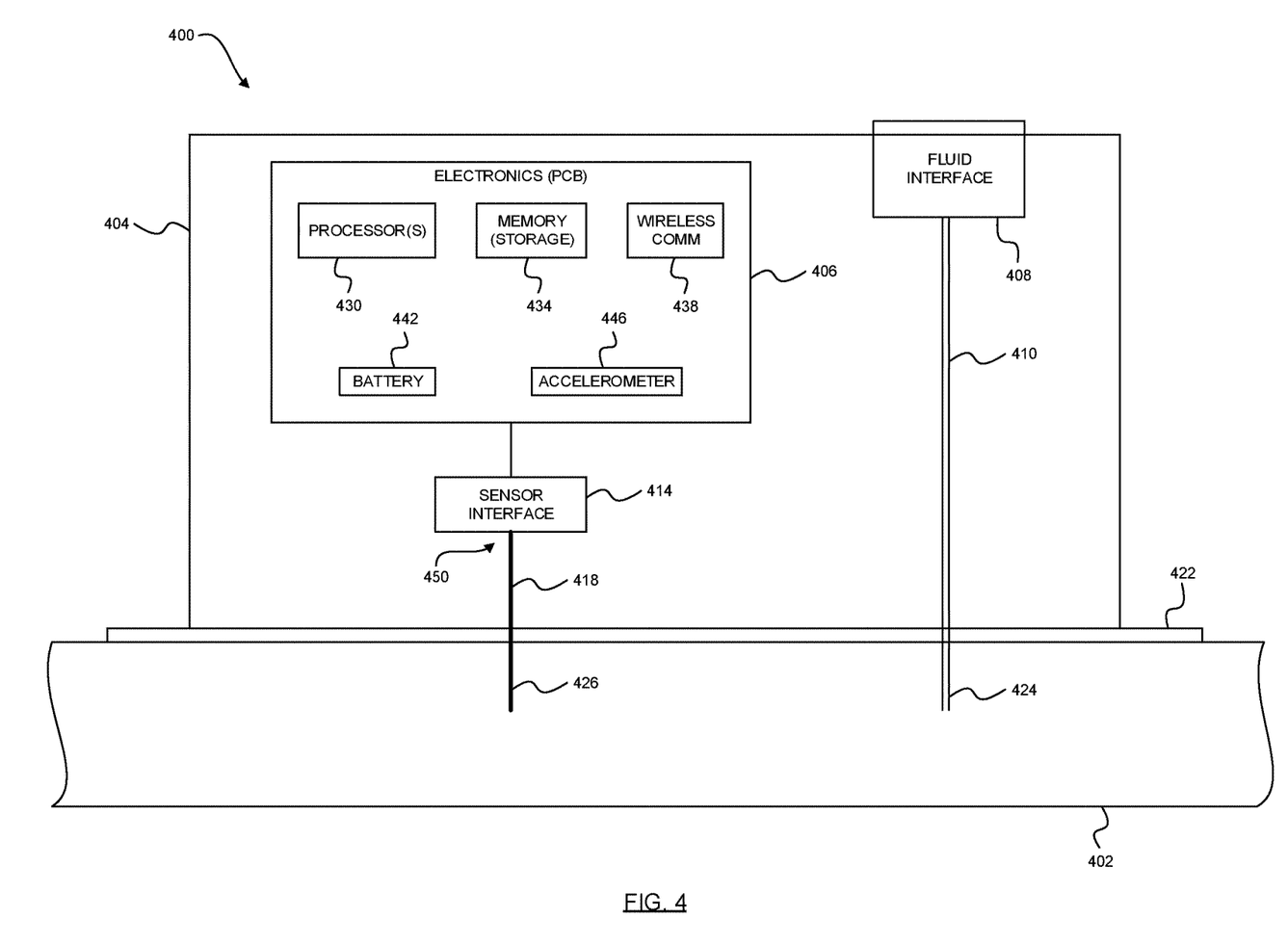
FIG. 4 is a schematic side view of an exemplary embodiment of an electronic medical device, after deployment and attachment to the body of the user.

FIG. 4 is a schematic side view of an electronic medical device 400 according to certain embodiments, after deployment and attachment to the body part 402 of a user. The electronic medical device 400 is one suitable implementation of the electronic device 102 shown in FIGS. 1-3. FIG. 4 depicts the housing 404 of the electronic medical device 400, along with various components, elements, and devices that are housed by, enclosed within, or attached to the housing 404. It should be appreciated that an embodiment of the electronic medical device 400 can include additional elements, components, and features that may provide conventional functionality that need not be described herein. Moreover, an embodiment of the electronic medical device 400 can include alternative elements, components, and features if so desired, as long as the intended and described functionality remains in place.

The embodiment of the electronic medical device 400 shown in FIG. 4 generally includes, without limitation: the housing 404; an electronics assembly 406 located within the housing 404; a fluid interface 408; a fluid delivery cannula 410 coupled to or included with the fluid interface 408; a sensor interface 414; an analyte sensor 418 coupled to or included with the sensor interface 414; and an adhesive patch 422 that secures the housing 404 to the body part 402 of the user. The housing 404 is suitably shaped, sized, and configured to house or support the electronics assembly 406, the fluid interface 408, the fluid delivery cannula 410, the sensor interface 414, the analyte sensor 418, and other components (not shown). FIG. 4 depicts the electronic medical device 400 after it has been deployed and affixed to the body part 402 of the user. Accordingly, the distal end 424 of the fluid delivery cannula 410 and the distal end 426 of the analyte sensor 418 are depicted in their inserted positions in the body part 402.

The electronics assembly 406 can be implemented as a printed circuit board to carry electronic components and elements that support operation of the electronic medical device 400, e.g., any number of discrete or integrated devices, electrical conductors or connectors, and the like. For example, the electronics assembly 406 may include the following items, without limitation: at least one processor 430; memory 434 to store data, processor-readable program instructions, and the like; a wireless communication module 438 to wirelessly receive and/or transmit signals, data, instructions, and the like; a battery 442 or other power source; and an accelerometer 446 to measure acceleration of the user-mountable electronic medical device 400. The electronics assembly 406 (or the components of the electronics assembly 406) can be electrically coupled to other elements of the electronic medical device 400 as needed to support the operation of the electronic medical device 400. For example, the electronics assembly 406 can be electrically coupled to at least the sensor interface 414. It should be appreciated that electrical connections to the electronics assembly 406 can be direct or indirect if so desired. Moreover, one or more components of the electronics assembly 406 may support wireless data communication internal to the electronic medical device 400.

The fluid interface 408 and the fluid delivery cannula 410 cooperate to form a fluid flow path for delivery of a fluid medicament to the user. The fluid interface 408, which may be accessible from outside the housing 404, may include a self-sealing septum or other type of fluid seal that accommodates a hollow needle for delivering the fluid medicament from a fluid source (e.g., a fluid reservoir of an external infusion pump device or mechanism) to the fluid delivery cannula 410. In certain embodiments (not depicted here), the electronic medical device 400 includes an internal fluid pump mechanism; in such embodiments, the fluid interface 408 may be optional. In either implementation, a fluid pump mechanism is controlled in an appropriate manner to regulate delivery of the fluid medicament (e.g., insulin) to the user, via the fluid delivery cannula 410.

The proximal end 450 of the analyte sensor 418 is electrically couplable to the sensor interface 414 to establish electrical connectivity between conductors of the analyte sensor 418 and the electronics assembly 406. Although depicted as a separate block in FIG. 4, the sensor interface 414 may be implemented on the electronics assembly 406 such that the analyte sensor 418 is electrically couplable to the electronics assembly 406 in a direct manner.

Referring again to the electronics assembly 406, each processor 430 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, a processor 430 or a plurality of processors 430 may be implemented as a combination of computing devices, e.g., a combination of a digital signal processor and a microprocessor, a plurality of microprocessors, one or more microprocessors in conjunction with a digital signal processor core, or any other such configuration.

The memory 434 may be realized as at least one memory element, device, module, or unit, such as: RAM memory, flash memory, EPROM memory, EEPROM memory, registers, a hard disk, a removable disk, optically readable media, or any other form of storage medium known in the art. In this regard, the memory 434 can be coupled to the at least one processor 430 such that the at least one processor 430 can read information from, and write information to, the memory 434. In the alternative, the memory 434 may be integral to the at least one processor 430. As an example, the at least one processor 430 and the memory 434 may reside in an ASIC. At least a portion of the memory 434 can be realized as a computer storage medium that is operatively associated with the at least one processor 430, e.g., a tangible, non-transitory computer-readable medium having computer-executable instructions stored thereon. The computer-executable instructions are configurable to be executed by the at least one processor 430 to cause the at least one processor 430 to perform certain tasks, operations, functions, and processes that are specific to the particular embodiment. In this regard, the memory 434 may represent one suitable implementation of such computer-readable media.

The wireless communication module 438 facilitates data communication between the electronic medical device 400 and other components as needed during the operation of the device 400. In the context of this description, the wireless communication module 438 can be employed to transmit or receive device-related control data, sensor data obtained in connection with operation of the analyte sensor 418, device-related status or operational data, calibration data, and the like. It should be appreciated that the particular configuration and functionality of the wireless communication module 438 can vary depending on the hardware platform and specific implementation of the electronic medical device 400. An embodiment of the electronic medical device 400 may support wireless data communication using various data communication protocols. For example, the wireless communication module 438 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Although not separately shown, embodiments of the electronic medical device 400 may also support one or more wired/cabled data communication protocols, including, without limitation: Ethernet; powerline; home network communication protocols; USB; IEEE 1394 (Firewire); hospital network communication protocols; and proprietary data communication protocols.

The battery 442 may be a single-use (disposable) battery or a rechargeable battery. The battery 442 represents the main power source of the electronic medical device 400, and is suitably configured to provide operating power to the at least one processor 430, the memory 434, the wireless communication module 438, the accelerometer 446, and other components (not shown) as needed. Accordingly, the battery 442 provides a relatively low amount of operating power during the standby or dormant state, and an increased amount of operating power during the active state. For example, the battery 442 provides sufficient power to the accelerometer 446 to support its operation during the standby or dormant state, such that the accelerometer 446 can respond to acceleration of the electronic medical device 400 and detect acceleration above the minimum acceleration threshold. As another example, the battery 442 provides sufficient standby power to the at least one processor 430 during the standby or dormant state, such that the at least one processor 430 can quickly "wake up" in response to the detection of acceleration above the minimum acceleration threshold. Moreover, the wireless communication module 438 can be held in a low power or "off" mode during the standby or dormant state, and switched to a high power or "on" mode for operation during the active state.

The accelerometer 446 is configured, arranged, and operated to measure acceleration of the host device, e.g., the electronic medical device 400. In certain embodiments, the accelerometer 446 is configured to generate a suitably formatted output (e.g., a trigger signal, an interrupt signal, a voltage level, an acceleration measurement or reading, a wakeup signal, a flag, a logical state, or the like) in response to detecting acceleration of the host device that is greater than a minimum acceleration threshold. Alternatively or additionally, the accelerometer 446 can be polled by the at least one processor 430 to obtain acceleration readings on demand, as needed, according to a designated schedule, periodically, etc. Other methodologies for detecting or measuring acceleration may be employed by embodiments of the host device. The accelerometer 446 can be implemented using any type of commercially available or custom accelerometer device, circuit, or package. The accelerometer 446 may be particularly specified or selected to accommodate the needs of the given application and to accurately and reliably detect acceleration above the desired minimum acceleration threshold while minimizing false positive detections. To this end, the electronics assembly 406 may include an appropriate calibration, biasing, or reference circuit or arrangement for the accelerometer 446, to ensure that the accelerometer 446 can detect acceleration in the desired range(s).

The minimum acceleration threshold can be selected to reduce the likelihood of accidental device activation. In this regard, the accelerometer can be chosen, calibrated, biased, or otherwise configured with an appropriate minimum acceleration threshold that prevents false triggers that may result from shipping, handling, dropping, transporting, and the like. Moreover, the minimum acceleration threshold can be selected to contemplate acceleration resulting from falls, traffic accidents, or other mishaps. Accordingly, the minimum acceleration threshold must be low enough to accurately and reliably detect the normally expected range of deployment acceleration experienced by the electronic device during deployment onto the body part of the user, while being high enough to avoid false triggering and accidental activation of the electronic device caused by events that are not associated with the deployment activity.

The at least one processor 430 controls certain operations of the electronic medical device 400. In particular, the at least one processor 430 is configured and arranged to receive the output generated by the accelerometer 446 and, in response to the received output, to transition the electronic medical device 400 from the dormant or standby state to the active state. In certain embodiments, actuation of the deployment device 104 of the electronic medical device 400 moves the device 400 toward the body part 402 of the user with a deployment acceleration that exceeds the minimum acceleration threshold. Accordingly, the accelerometer 446 (which is calibrated, biased, or otherwise designed to detect at least the minimum acceleration threshold) reacts to the deployment acceleration, and generates an output that causes the at least one processor 430 to activate, wake up, turn on, or otherwise transition the electronic medical device 400 into its active state for normal post-deployment operation. The output generated by the accelerometer 446 may serve as an interrupt or wakeup signal for the at least one processor 430. Thereafter, the at least one processor 430 can proceed with an appropriate activation procedure to, for example, power up the wireless communication module 438 and other components of the electronic medical device 400.

Figure 5:
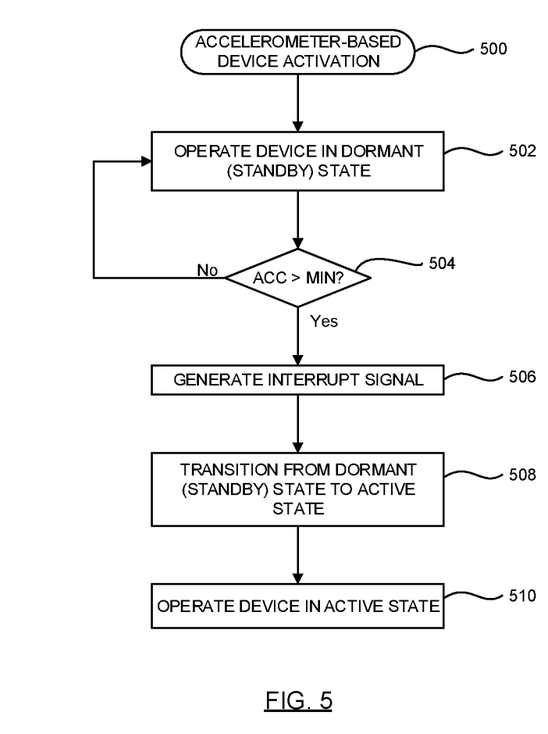
FIG. 5 is a flow chart that illustrates an accelerometer-based device activation process according to certain embodiments.

FIG. 5 is a flow chart that illustrates an accelerometer-based device activation process 500 according to certain embodiments. It should be appreciated that an implementation of the process 500 may include any number of additional or alternative tasks, the tasks shown in FIG. 5 need not be performed in the illustrated order, and the process 500 may be incorporated into a more comprehensive procedure or process having additional functionality not described in detail herein. Moreover, one or more of the tasks shown in FIG. 5 could be omitted from an embodiment of the process 500 as long as the intended overall functionality remains intact.

In accordance with the process 500, the host electronic device is operated in a dormant or standby state (task 502). An accelerometer onboard the host electronic device monitors the acceleration of the device, and checks whether a minimum acceleration threshold has been exceeded (query task 504). If the acceleration of the host electronic device is greater than the minimum acceleration threshold (the "Yes" branch of query task 504), then the accelerometer generates an output, such as an interrupt signal (task 506). Alternatively or additionally, the accelerometer can be polled by the at least one processor such that periodic acceleration measurements or readings can be obtained and checked. In such embodiments, the at least one processor may poll the accelerometer according to a schedule to determine whether the device experienced acceleration above the minimum acceleration threshold since the last polling time. If acceleration of the host electronic device does not exceed the minimum acceleration threshold (the "No" branch of query task 504), then the host device remains in the dormant or standby state.

The interrupt signal (and/or some other means for detecting acceleration above the threshold value) triggers a transition from the dormant (standby) state to the active state (task 508). As mentioned above, the interrupt signal may cause the at least one processor to wake up and change certain power settings, features, or controls to place the host device into its normal operating mode. Thereafter, the host device continues to operate in the active state (task 510). After the host device transitions to the active state, any further output from the accelerometer can be ignored or disregarded.

The use of an accelerometer to activate a user-mountable electronic device is cost efficient, reliable, and easy to implement. Only one component is required to be onboard the host device, e.g., an accelerometer chip or circuit device, which reduces parts count relative to other schemes and methodologies that require multiple components (such as a two-part sensor assembly).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A user-mountable electronic device comprising:
    a housing;
    an accelerometer to measure acceleration of the user-mountable electronic device, the accelerometer located within the housing, and the accelerometer configured to generate an output in response to detecting acceleration of the user-mountable electronic device that is greater than a minimum acceleration threshold; and
    at least one processor to control operation of the user-mountable electronic device, the at least one processor located within the housing, and the at least one processor configured to receive the output generated by the accelerometer and, in response thereto, to transition from a dormant or standby state of the user-mountable electronic device to an active state of the user-mountable electronic device;
    wherein the minimum acceleration threshold is based on an acceleration to be experienced by the accelerometer when the housing is moved toward a body part of a user with a deployment acceleration.

2. A user-mountable electronic device comprising:
    a housing;
    an accelerometer to measure acceleration of the user-mountable electronic device, the accelerometer located within the housing, and the accelerometer configured to generate an output in response to detecting acceleration of the user-mountable electronic device that is greater than a minimum acceleration threshold; and
    at least one processor to control operation of the user-mountable electronic device, the at least one processor located within the housing, and the at least one processor configured to receive the output generated by the accelerometer and, in response thereto, to transition from a dormant or standby state of the user-mountable electronic device to an active state of the user-mountable electronic device;
    wherein:
    the user-mountable electronic device is deployable onto a body part of a user, via a deployment device that is compatible with the user-mountable electronic device; and
    actuation of the deployment device moves the user-mountable electronic device toward the body part of the user with a deployment acceleration that exceeds the minimum acceleration threshold.

3. The user-mountable electronic device of claim 2, wherein:
    the user-mountable electronic device comprises an analyte sensor; and
    the actuation of the deployment device initiates insertion of the analyte sensor into the user.

4. The user-mountable electronic device of claim 2, wherein:
    the user-mountable electronic device comprises a fluid delivery cannula; and
    the actuation of the deployment device initiates insertion of the fluid delivery cannula into the user.

5. The user-mountable electronic device of claim 2, further comprising an adhesive patch on a bottom surface of the housing, wherein the actuation of the deployment device moves an exposed adhesive surface of the adhesive patch into contact with the body part of the user to affix the user-mountable electronic device to the body part of the user.

6. The user-mountable electronic device of claim 1, wherein the output generated by the accelerometer comprises an interrupt or wakeup signal for the at least one processor.

7. The user-mountable electronic device of claim 1, wherein the dormant or standby state is a low power state, and the active state is a normal power consumption state.

8. The user-mountable electronic device of claim 1, wherein the user-mountable electronic device comprises at least one of a transdermal medicament delivery device or a transdermal analyte sensor device.

9. The user-mountable electronic device of claim 1, wherein the user-mountable electronic device comprises:
    a continuous glucose sensor that is insertable into a user to obtain sensor glucose measurements; and
    a fluid delivery cannula that is insertable into the user to deliver insulin to the user.

10. The user-mountable electronic device of claim 1, wherein the accelerometer is selected, calibrated, biased, or otherwise configured with an appropriate minimum acceleration threshold that is low enough to detect an expected range of deployment acceleration experienced by the user-mountable electronic device during deployment onto the body part of the user, while being high enough to avoid triggering activation of the electronic device from typical falls or traffic accidents.

11. A system comprising:
    a user-mountable electronic device that is deployable onto a body part of a user, the user-mountable electronic device comprising:
        a housing;
        an accelerometer to measure acceleration of the user-mountable electronic device, the accelerometer located within the housing, and the accelerometer configured to generate an output in response to detecting acceleration of the user-mountable electronic device that is greater than a minimum acceleration threshold; and
        at least one processor to control operation of the user-mountable electronic device, the at least one processor located within the housing, and the at least one processor configured to receive the output generated by the accelerometer and, in response thereto, to transition from a dormant or standby state of the user-mountable electronic device to an active state of the user-mountable electronic device; and
    a deployment device compatible with the user-mountable electronic device, wherein the deployment device is actuatable to move the user-mountable electronic device toward the body part of the user with a deployment acceleration that exceeds the minimum acceleration threshold.

12. The system of claim 11, wherein:
the user-mountable electronic device comprises an analyte sensor; and
actuation of the deployment device initiates insertion of the analyte sensor into the user.

13. The system of claim 11, wherein:
the user-mountable electronic device comprises a fluid delivery cannula; and
actuation of the deployment device initiates insertion of the fluid delivery cannula into the user.

14. The system of claim 11, further comprising an adhesive patch on a bottom surface of the housing, wherein actuation of the deployment device moves an exposed adhesive surface of the adhesive patch into contact with the body part of the user to affix the user-mountable electronic device to the body part of the user.

15. The system of claim 11, wherein the output generated by the accelerometer comprises an interrupt or wakeup signal for the at least one processor.

16. The system of claim 11, wherein the dormant or standby state is a low power state, and the active state is a normal power consumption state.

17. The system of claim 11, wherein the user-mountable electronic device comprises a transdermal medicament delivery device or a transdermal analyte sensor device.

18. The system of claim 11, wherein the output generated by the accelerometer comprises an acceleration measurement.

19. The system of claim 11, wherein the user-mountable electronic device comprises:
a continuous glucose sensor that is insertable into the user to obtain sensor glucose measurements; and
a fluid delivery cannula that is insertable into the user to deliver insulin to the user.

20. The system of claim 11, wherein:
the user-mountable electronic device and the deployment device are coupled together as a unit before actuation of the deployment device;
the user-mountable electronic device operates in the dormant or standby state before actuation of the deployment device;
the deployment device decouples from the user-mountable electronic device after actuation of the deployment device; and
the user-mountable electronic device operates in the active state after actuation of the deployment device.

* * * * *